(12) United States Patent
Cao et al.

(10) Patent No.: US 12,306,120 B2
(45) Date of Patent: May 20, 2025

(54) APPARATUS AND METHOD FOR BIOLOGICAL ANALYTE STUDYING USING X-RAY FLUORESCENCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 244 days.

(21) Appl. No.: 18/195,984

(22) Filed: May 11, 2023

(65) Prior Publication Data

US 2023/0280292 A1   Sep. 7, 2023

Related U.S. Application Data

(63) Continuation of application No. PCT/CN2020/131468, filed on Nov. 25, 2020.

(51) Int. Cl.
*G01N 23/223* (2006.01)
*G01N 33/58* (2006.01)

(52) U.S. Cl.
CPC ........ *G01N 23/223* (2013.01); *G01N 33/582* (2013.01); *G01N 2223/612* (2013.01)

(58) Field of Classification Search
CPC .. G01N 23/085; G01N 2001/007; G01N 1/00; G01N 1/28; G01N 1/2806; G01N 23/20; G01N 23/20058; G01N 23/20075; G01N 23/20091; G01N 23/205; G01N 23/2055; G01N 23/207; G01N 23/2076;
(Continued)

(56) References Cited

U.S. PATENT DOCUMENTS

| 6,751,287 | B1 * | 6/2004 | Kalyon | ................. | G01N 23/20 378/71 |
| 7,796,726 | B1 | 9/2010 | Gendreau et al. | | |
| 2015/0276632 | A1 | 10/2015 | Peterson et al. | | |

FOREIGN PATENT DOCUMENTS

| CN | 102692426 A | 9/2012 |
| CN | 103399026 A | 11/2013 |

(Continued)

OTHER PUBLICATIONS

Pushie, M. Jake, et al. "Elemental and chemically specific X-ray fluorescence imaging of biological systems." Chemical Reviews 114.17 (2014): 8499-8541. figure 26.
(Continued)

*Primary Examiner* — Don K Wong
(74) *Attorney, Agent, or Firm* — IPro, PLLC

(57) ABSTRACT

Disclosed herein is an apparatus, comprising: an X-ray source; an X-ray detector; wherein the X-ray source is configured to direct an X-ray beam toward a surface at a glancing angle at which the X-ray beam undergoes total external reflection by the surface; wherein a first biological analyte is immobilized to the surface and a first element is attached to the first biological analyte; wherein the X-ray beam is capable of causing emission of characteristic X-rays of the first element; wherein the X-ray detector is configured to receive the characteristic X-rays of the first element but not the X-ray beam reflected by the surface.

20 Claims, 11 Drawing Sheets

(58) Field of Classification Search
CPC ............... G01N 23/22; G01N 23/2202; G01N 23/2204; G01N 23/2206; G01N 23/221; G01N 23/223; G01N 30/00; G01N 2333/00; G21K 2201/061; G21K 1/00; G21K 1/06; G21K 1/067; G21K 5/00; G21K 5/04; G21K 7/00; G21K 2201/06
See application file for complete search history.

(56) References Cited

FOREIGN PATENT DOCUMENTS

| | | |
|---|---|---|
| CN | 106404886 A | 2/2017 |
| CN | 106996941 A | 8/2017 |
| CN | 107209130 A | 9/2017 |
| GB | 2583978 A | 11/2020 |
| JP | 2020020689 A | 2/2020 |
| TW | 200827703 A | 7/2008 |

OTHER PUBLICATIONS

Uo, Motohiro, Takahiro Wada, and Tomoko Sugiyama. "Applications of X-ray fluorescence analysis (XRF) to dental and medical specimens." Japanese Dental Science Review 51.1 (2015): 2-9.
Li, Liang, et al. "Full-field fan-beam x-ray fluorescence computed tomography with a conventional x-ray tube and photon-counting detectors for fast nanoparticle bioimaging." Optical Engineering 56.4 (2017): 043106-043106.

* cited by examiner

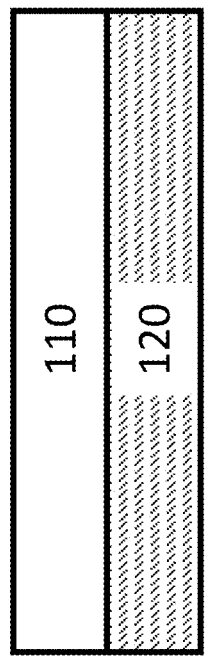

APPARATUS AND METHOD FOR BIOLOGICAL ANALYTE STUDYING USING X-RAY FLUORESCENCE

BACKGROUND

X-ray fluorescence (XRF) is the emission of characteristic X-rays from a material that has been excited by, for example, exposure to high-energy X-rays or gamma rays. An electron on an inner orbital of an atom may be ejected, leaving a vacancy on the inner orbital, if the atom is exposed to X-rays or gamma rays with photon energy greater than the ionization potential of the electron. When an electron on an outer orbital of the atom relaxes to fill the vacancy on the inner orbital, an X-ray (fluorescent X-ray or secondary X-ray) is emitted. The emitted X-ray has a photon energy equal the energy difference between the outer orbital and inner orbital electrons.

For a given atom, the number of possible relaxations is limited. As shown in FIG. 1A, when an electron on the L orbital relaxes to fill a vacancy on the K orbital (L→K), the fluorescent X-ray is called Kα. The fluorescent X-ray from M→K relaxation is called Kβ. As shown in FIG. 1B, the fluorescent X-ray from M→L relaxation is called Lα, and so on.

Analyzing the fluorescent X-ray spectrum can identify the elements in a sample because each element has orbitals of characteristic energy. The fluorescent X-ray can be analyzed either by sorting the energies of the photons (energy-dispersive analysis) or by separating the wavelengths of the fluorescent X-ray (wavelength-dispersive analysis). The intensity of each characteristic energy peak is directly related to the amount of each element in the sample.

Proportional counters or various types of solid-state detectors (PIN diode, Si(Li), Ge(Li), Silicon Drift Detector SDD) may be used in energy dispersive analysis. These detectors are based on the same principle: an incoming photon of X-ray ionizes a large number of detector atoms with the amount of charge carriers produced being proportional to the energy of the incoming photon of X-ray. The charge carriers are collected and counted to determine the energy of the incoming photon of X-ray and the process repeats itself for the next incoming photon of X-ray. After detection of many photon of X-rays, a spectrum may be compiled by counting the number of photon of X-rays as a function of their energy.

SUMMARY

Disclosed herein is an apparatus, comprising: an X-ray source; an X-ray detector; wherein the X-ray source is configured to direct an X-ray beam toward a surface at a glancing angle at which the X-ray beam undergoes total external reflection by the surface; wherein a first biological analyte is immobilized to the surface and a first element is attached to the first biological analyte; wherein the X-ray beam is capable of causing emission of characteristic X-rays of the first element; wherein the X-ray detector is configured to receive the characteristic X-rays of the first element but not the X-ray beam reflected by the surface.

According to an embodiment, the apparatus further comprises the surface.

According to an embodiment, the surface is an external surface of a substrate.

According to an embodiment, the surface is an external surface of a film with a thickness less than 10 micrometers.

According to an embodiment, the film is a metal film.

According to an embodiment, the film is an epitaxial silicon film.

According to an embodiment, no X-ray beam from the X-ray source incident on the surface does not undergo total external reflection at the surface.

According to an embodiment, the apparatus further comprises a slit or a collimator in front of the X-ray source.

According to an embodiment, the X-ray beam directed to the surface is a fan beam.

According to an embodiment, the X-ray beam directed to the surface is a collimated beam.

According to an embodiment, the X-ray detector is configured to detect the first element by determining energies of photons of the characteristic X-rays of the first element.

According to an embodiment, the X-ray detector is configured to count numbers of the photons of the characteristic X-rays of the first element.

According to an embodiment, the surface is not at an interface with a liquid.

According to an embodiment, the first biological analyte is a protein or a nucleic acid.

According to an embodiment, the first element is attached to the first biological analyte by a ligand.

According to an embodiment, the apparatus further comprises the first biological analyte.

According to an embodiment, the apparatus further comprises a filter configured to prevent photons of X-ray having energies above a threshold and emitted by the X-ray source from reaching the surface.

According to an embodiment, the X-ray detector is configured not to distinguish photons of the X-ray beam and photons of the characteristic X-rays of the first element.

According to an embodiment, the first element has an atom number larger than 20.

According to an embodiment, the first element has an atom number larger than 26.

According to an embodiment, the X-ray beam is capable of causing emission of characteristic X-rays of a second element attached to a second biological analyte immobilized to the surface.

According to an embodiment, the X-ray detector is configured to receive a combination of the characteristic X-rays of the first element and the characteristic X-rays of the second element.

According to an embodiment, the X-ray detector is configured to detect the second element by determining energies of photons of the characteristic X-rays of the second element.

Disclosed herein is a method comprising: directing an X-ray beam toward a surface at a glancing angle so that the X-ray beam undergoes total external reflection by the surface, wherein a first biological analyte is immobilized to the surface and a first element is attached to the first biological analyte and wherein the X-ray beam causes emission of characteristic X-rays of the first element; receiving, with an X-ray detector, the characteristic X-rays of the first element but not the X-ray beam reflected by the surface.

BRIEF DESCRIPTION OF FIGURES

FIG. 3A-FIG. 3C each schematically show a cross-sectional view of an X-ray detector, according to an embodiment.

DETAILED DESCRIPTION

Figure 1A:
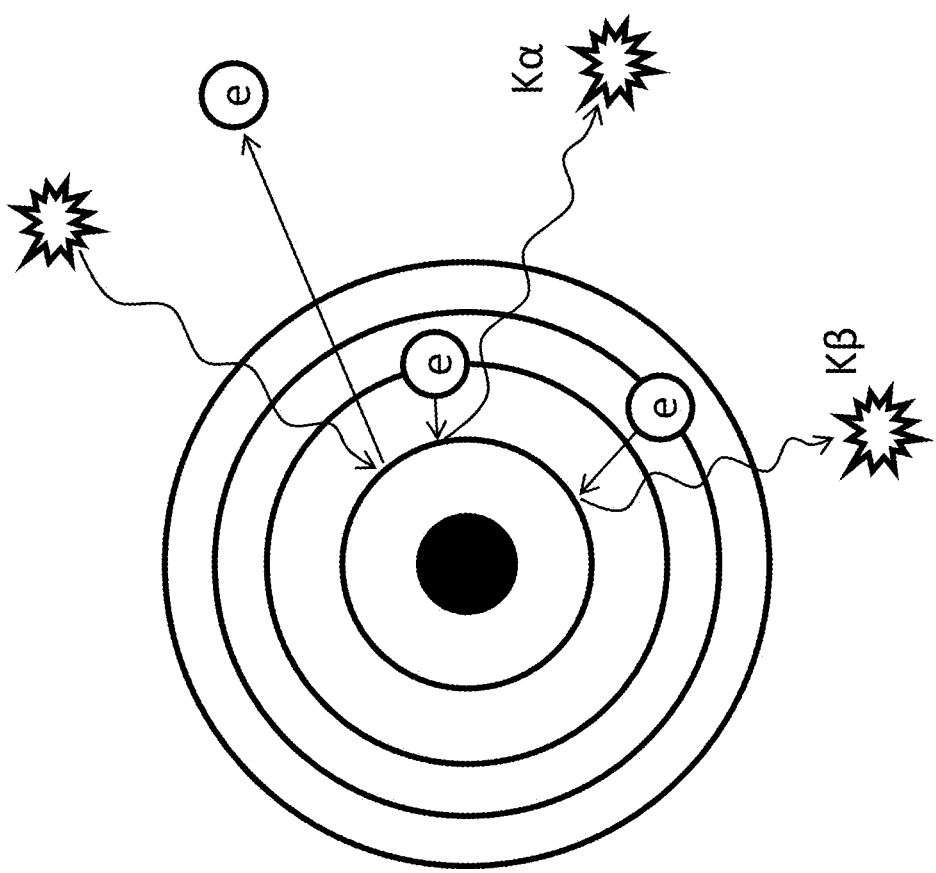
FIG. 1A and FIG. 1B schematically show mechanisms of X-ray fluorescence (XRF).
Figure 1B:
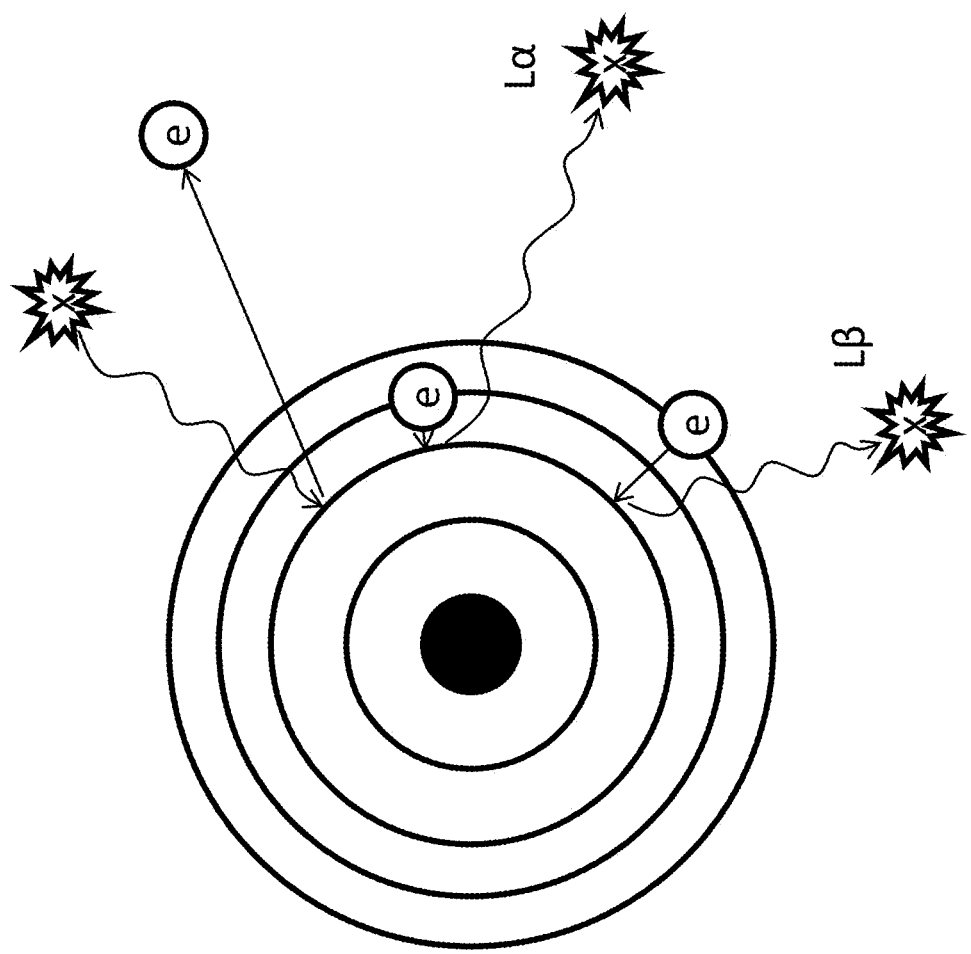
Figure 2:
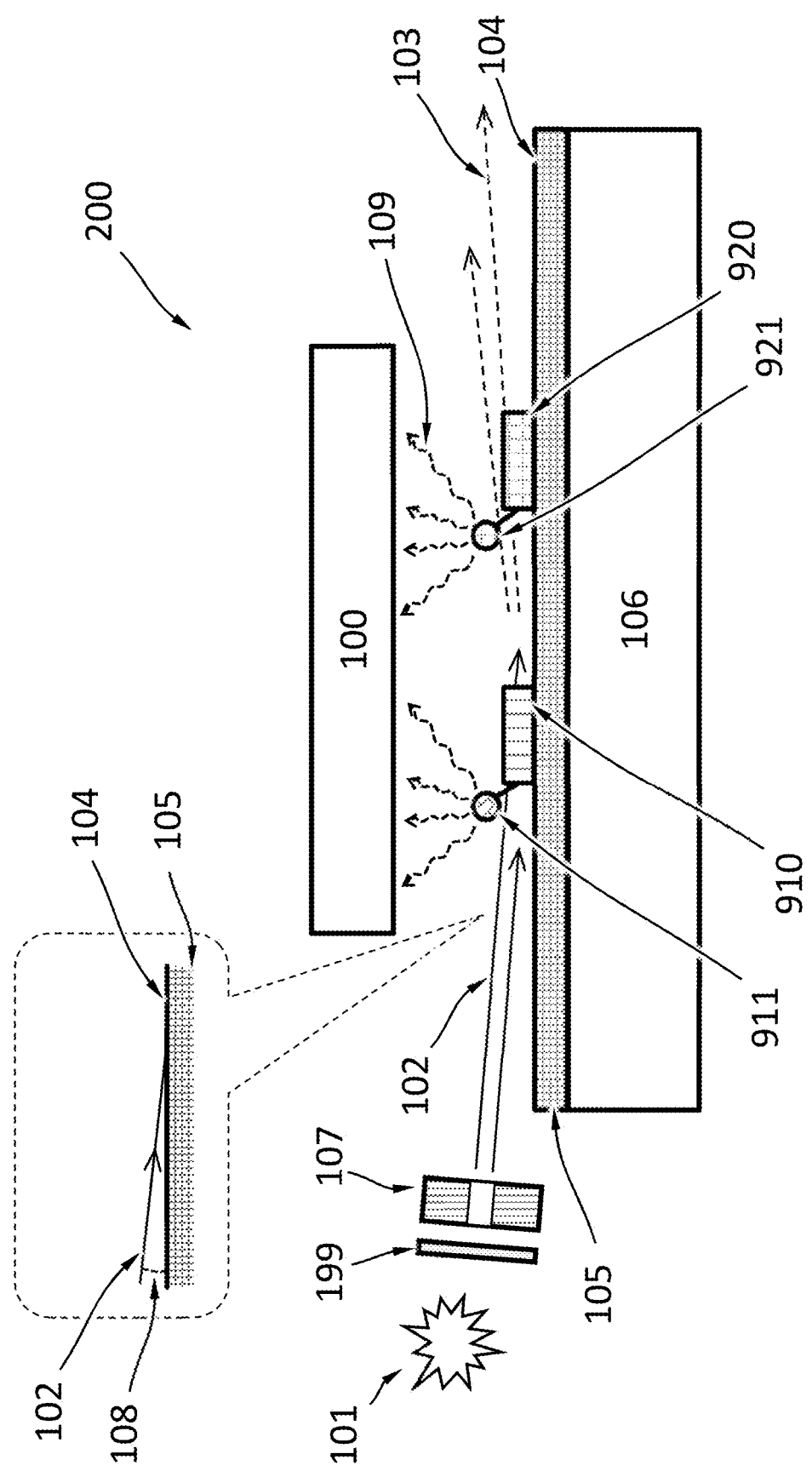
FIG. 2 schematically shows apparatus, according to an embodiment.

X-ray fluorescence (XRF) can be used to study biological samples by detecting elements attached to biological analytes. FIG. 2 schematically shows an apparatus 200 configured to study biological analytes using XRF with a configuration of total external reflection (TER). The apparatus 200 may include an X-ray detector 100 and an X-ray source 101.

The X-ray source 101 is configured to direct an X-ray beam 102 toward a surface 104 at a glancing angle 108 at which the X-ray beam 102 undergoes total external reflection by the surface 104, according to an embodiment. The glancing angle 108 is an angle between the X-ray beam 102 and the surface 104, as shown in FIG. 2. The upper limit of the magnitude of the glancing angle 108 may depend on the wavelength of the X-ray beam 102 and characteristics (e.g., material) of the surface 104. When the glancing angle 108 has a magnitude smaller than the upper limit, the X-ray beam 102 undergoes total external reflection. In an aspect, the X-ray source 101 is configured so that no X-ray beam from the X-ray source 101 does not undergo total reflection at the surface 104. The apparatus 200 may include a slit or a collimator 107 in front of the X-ray source 101. The X-ray beam 102 may be a fan beam or a collimated beam. The apparatus 200 may further include a filter 199 configured to prevent photons of X-ray having energies above a threshold and emitted by the X-ray source 101 from reaching the surface 104.

The surface 104 may be an external surface of a substrate 106. The surface 104 may an external surface of a film 105 with a thickness less than 10 micrometers. For example, the film 105 may be a metal film or an epitaxial silicon film. The surface 104 may be part of the apparatus 200. In an aspect, the surface 104 is not at an interface with a liquid. In an aspect, a first biological analyte 910 is immobilized to the surface 104 and a first element 911 is attached to the first biological analyte 910. The first element 911 may be attached to the first biological analyte 910 by a ligand. The first element 911 may have an atom number larger than 20, or larger than 26. The first biological analyte 910 may be part of the apparatus 200. The first biological analyte 910 may be a protein or a nucleic acid.

In an aspect, the X-ray beam 102 is capable of causing the first element 911 to emit its characteristic X-rays 109. The X-ray detector 100 is configured to receive the characteristic X-rays 109 but not the X-ray beam 103 reflected by the surface 104, as shown in FIG. 2. The position of the X-ray detector 100 is not necessarily fixed. For example, the X-ray detector 100 may be movable toward and away from the surface 104 or may be rotatable relative to the surface 104. In an aspect, the X-ray detector 100 is configured not to distinguish photons of the X-ray beam 102 and photons of the characteristic X-rays 109, if the X-ray detector 100 receives both. The X-ray detector 100 may be configured to detect the first element 911 by determining energies of photons of the characteristic X-rays 109, or be configured to count numbers of the photons of the characteristic X-ray 109.

There may be a second biological analyte 920 immobilized to the surface 104 and a second element 921 attached to the second biological analyte 920. The second biological analyte 920 may not be spatially separate from the first biological analyte 910. If the second biological analyte 920 is present, the X-ray beam 102 is capable of causing the second element 921 to emit its characteristic X-rays. The X-ray detector 100 may be arranged at about the same distance or different distances from the first biological analyte 910 and the second biological analyte 920. The X-ray detector 100 may receive a combination of the characteristic X-rays of the first element 911 and the characteristic X-rays of the second element 921. The X-ray detector 100 may detect the second element by determining energies of photons of the characteristic X-rays of the second element 921.

FIG. 3A schematically shows a cross-sectional view of the X-ray detector 100, according to an embodiment. The X-ray detector 100 may include an X-ray absorption layer 110 and an electronics layer 120 (e.g., an ASIC) for processing or analyzing electrical signals incident X-ray generates in the X-ray absorption layer 110. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 3B:
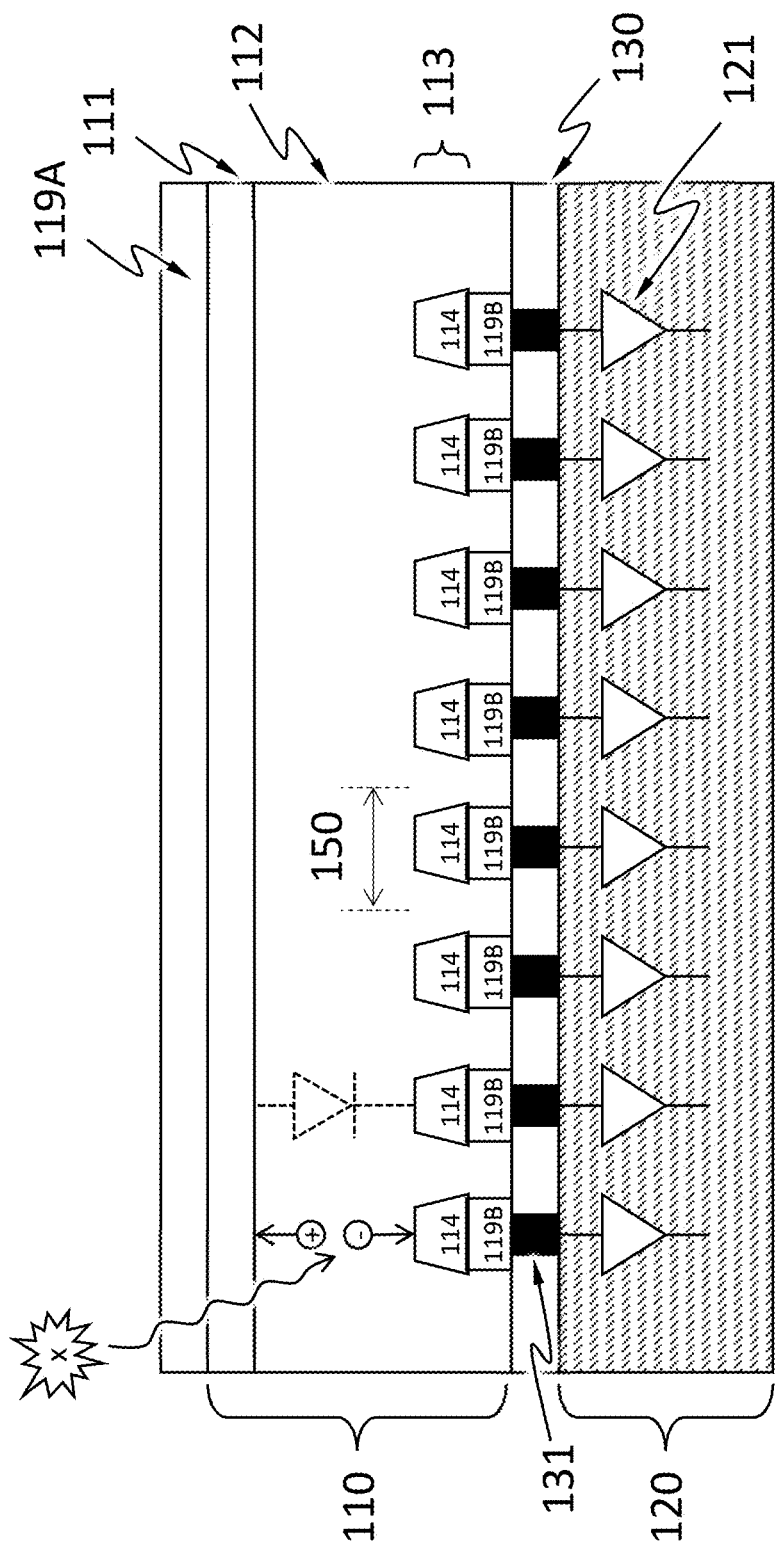

As shown in a detailed cross-sectional view of the X-ray detector 100 in FIG. 3B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 3B, each of the discrete regions 114 of the second doped region 113 forms a diode with the first doped region 111 and the optional intrinsic region 112. Namely, in the example in FIG. 3B, the X-ray absorption layer 110 has a plurality of diodes having the first doped region 111 as a shared electrode. The first doped region 111 may also have discrete portions.

When a photon of X-ray hits the X-ray absorption layer 110 including diodes, the photon of X-ray may be absorbed and generate one or more charge carriers by a number of mechanisms. A photon of X-ray may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single photon of X-ray are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a photon of X-ray incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a photon of X-ray incident therein flow to the discrete region 114. Namely, less than 2%, less than 1%, less than 0.1%, or less than 0.01% of these charge carriers flow beyond the pixel.

Figure 3C:
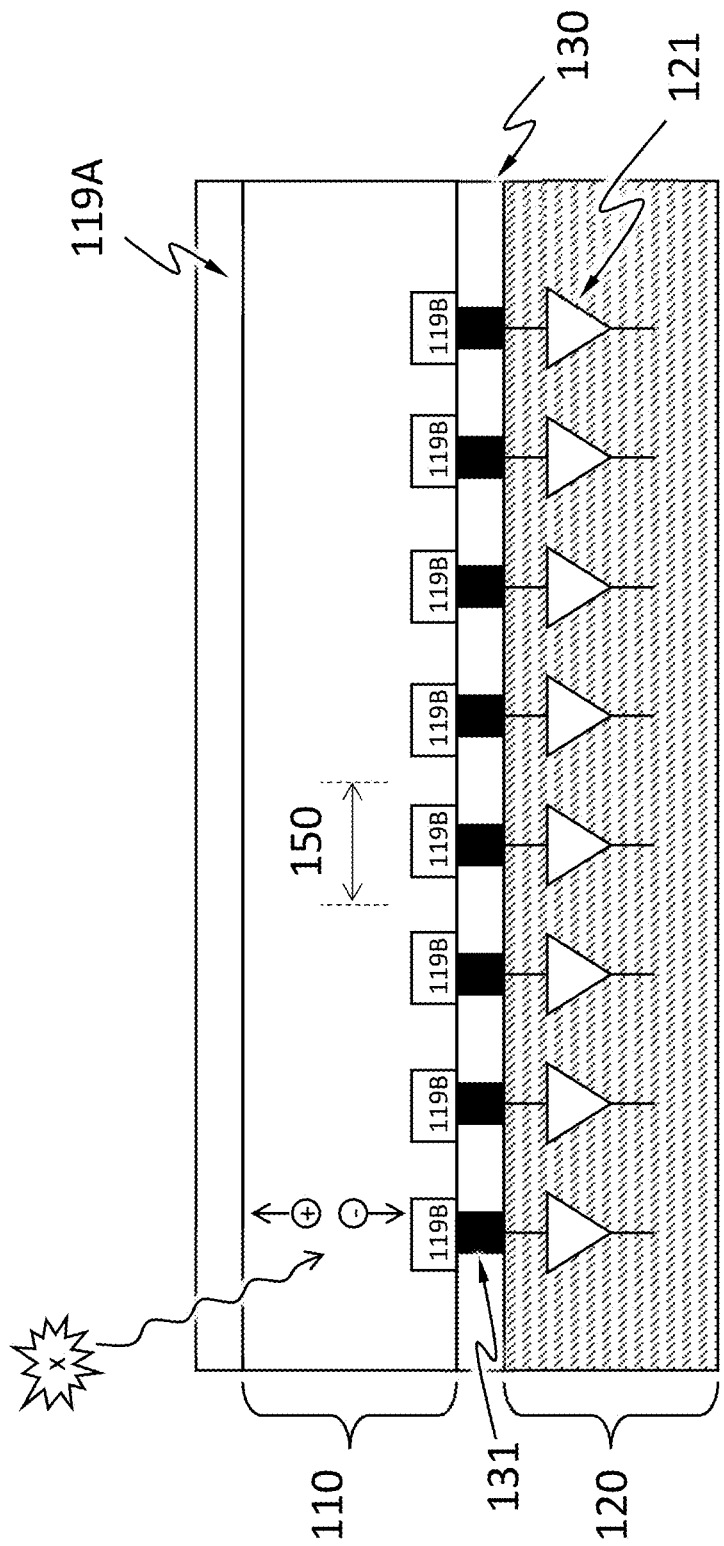

As shown in an alternative detailed cross-sectional view of the X-ray detector 100 in FIG. 3C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When a photon of X-ray hits the X-ray absorption layer 110 including a resistor but not diodes, it may be absorbed and generate one or more charge carriers by a number of mechanisms. A photon of X-ray may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single photon of X-ray are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by a photon of X-ray incident around the footprint of one of these discrete portions of the electrical contact 119B are not substantially shared with another of these discrete portions of the electrical contact 119B. The pixel 150 associated with a discrete portion of the electrical contact 119B may be an area around the discrete portion in which substantially all (more than 98%, more than 99.5%, more than 99.9% or more than 99.99% of) charge carriers generated by a photon of X-ray incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by photons of X-ray incident on the X-ray absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 4:
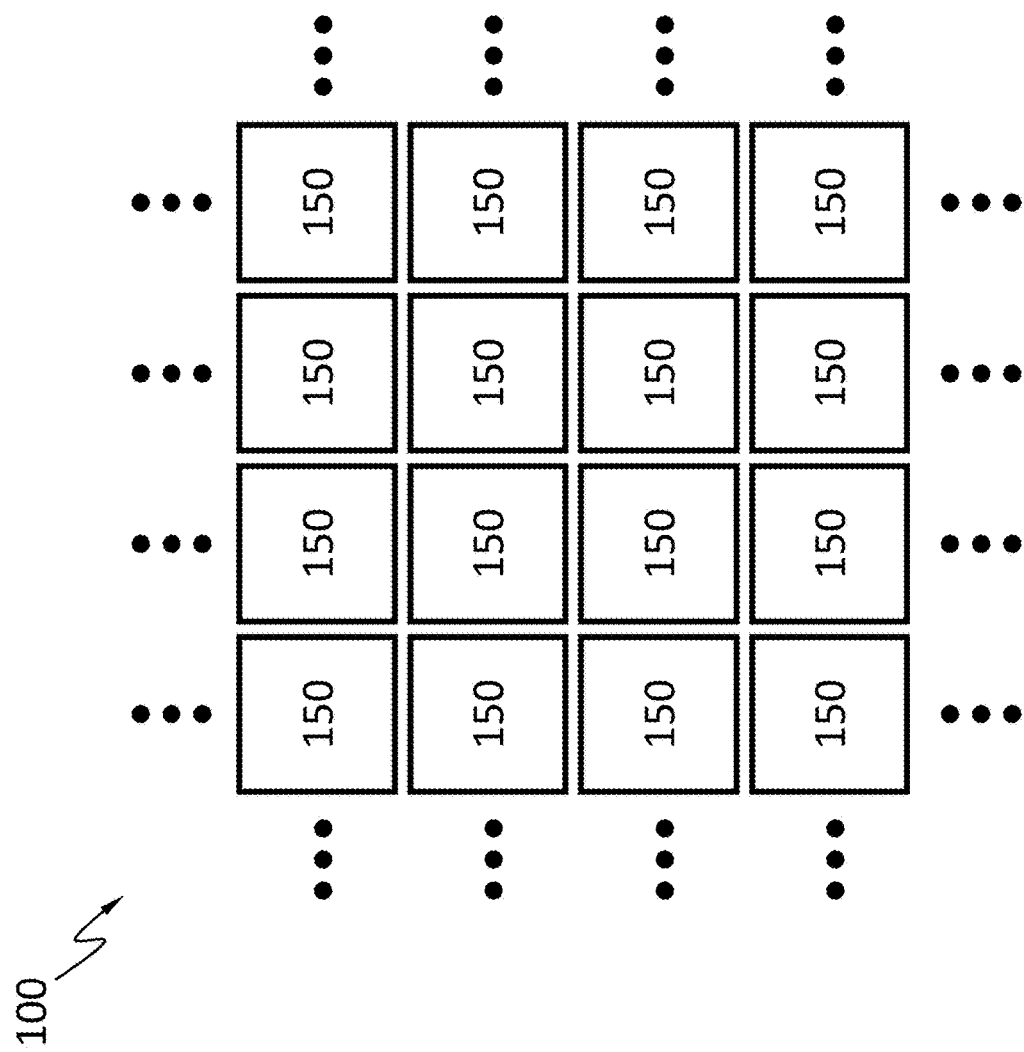
FIG. 4 schematically a top view of a portion of the X-ray detector, according to an embodiment.

FIG. 4 schematically a top view of a portion of the X-ray detector 100 with an array of pixels 150, according to an embodiment. The array may be a rectangular array, a honeycomb array, a hexagonal array or any other suitable array. Each pixel 150 may be configured to detect a photon of X-ray incident thereon and determine the energy of the photon of X-ray. For example, each pixel 150 is configured to detect and count numbers of characteristic photons of X-ray emitted from the first element 911 and the second element 921 incident thereon, within a period of time, but not to count photons with energy different from the photons of the characteristic X-rays. All the pixels 150 may be configured to detect and count the numbers of characteristic photons of X-ray incident thereon within a plurality of bins of energy within the same period of time. According to an embodiment, detecting the characteristic of the first biological analyte 910 based on the characteristic X-rays of the first element 911 and the characteristic of the second biological analyte 920 based on the characteristic X-rays of the second element 921 comprises receiving a combination of the characteristic X-rays of the first element 911 and the characteristic X-rays of the second element 921, and determining the energies of photons of X-ray in the combination. Each pixel 150 may have its own analog-to-digital converter (ADC) configured to digitize an analog signal representing the energy of an incident photon of X-ray into a digital signal. For XRF applications, an ADC with a 10-bit resolution or higher is useful. Each pixel 150 may be configured to measure its dark current, such as before or concurrently with each photon of X-ray incident thereon. Each pixel 150 may be configured to deduct the contribution of the dark current from the energy of the photon of X-ray incident thereon. The pixels 150 may be configured to operate in parallel. For example, when one pixel 150 measures an incident photon of X-ray, another pixel 150 may be waiting for a photon of X-ray to arrive. The pixels 150 may not have to be individually addressable.

The X-ray detector 100 may have at least 100, 2500, 10000, or more pixels 150. The X-ray detector 100 may be configured to add the numbers of photons of X-ray for the bins of the same energy range counted by all the pixels 150. For example, the X-ray detector 100 may add the numbers the pixels 150 stored in a bin for energy from 70 KeV to 71 KeV, add the numbers the pixels 150 stored in a bin for energy from 71 KeV to 72 KeV, and so on. In one embodiment, the characteristic photons of X-ray from the first element 911 and the second element 921 whose energies are within a first range are counted and added into in related bins. The X-ray detector 100 may compile the added numbers for the bins as a spectrum of intensity of the characteristic photons of X-ray incident on the X-ray detector 100.

Figure 5A:
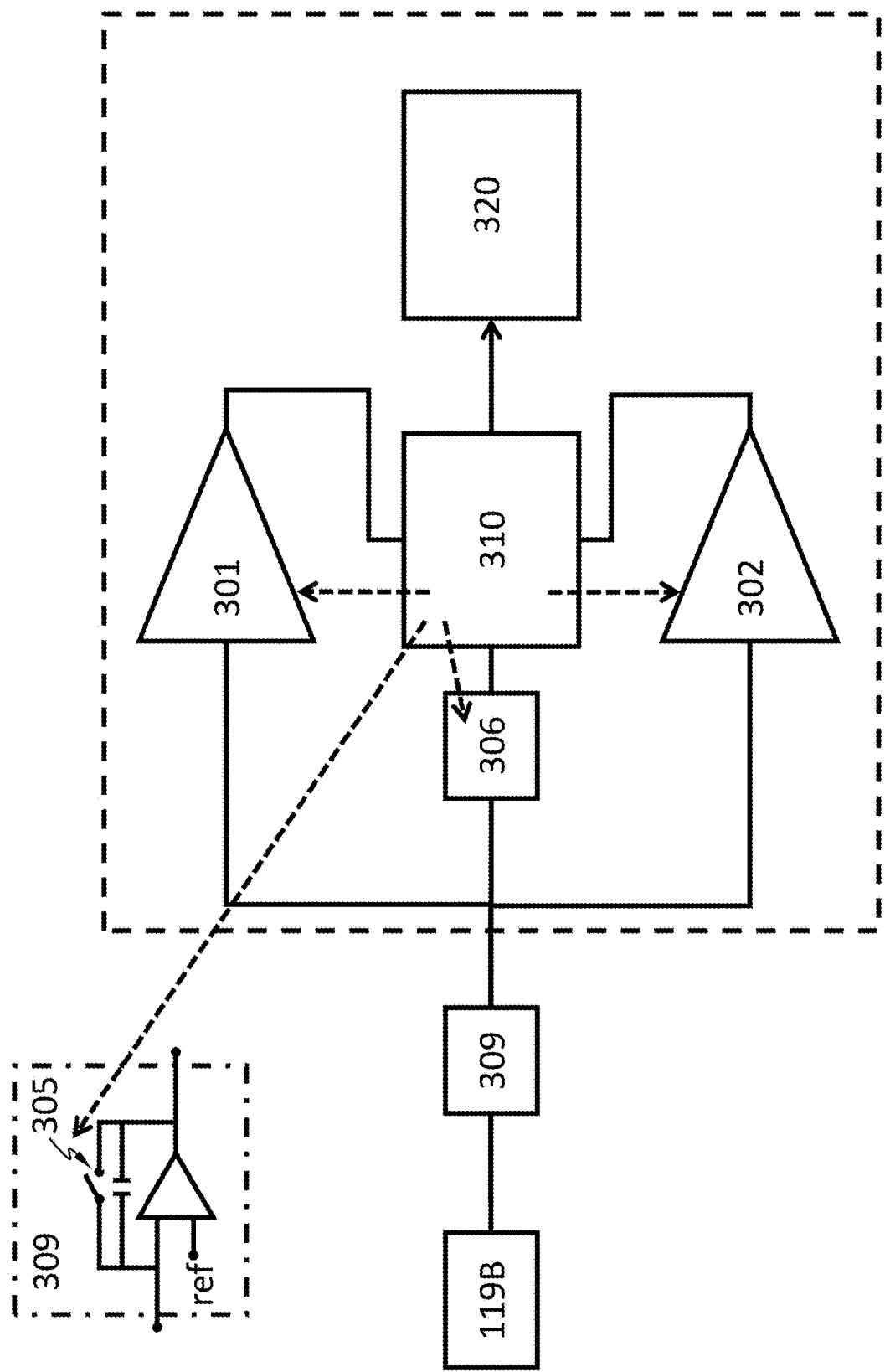
FIG. 5A-FIG. 5B each schematically show a component diagram of an electronic system of the X-ray detector, according to an embodiment.
Figure 5B:
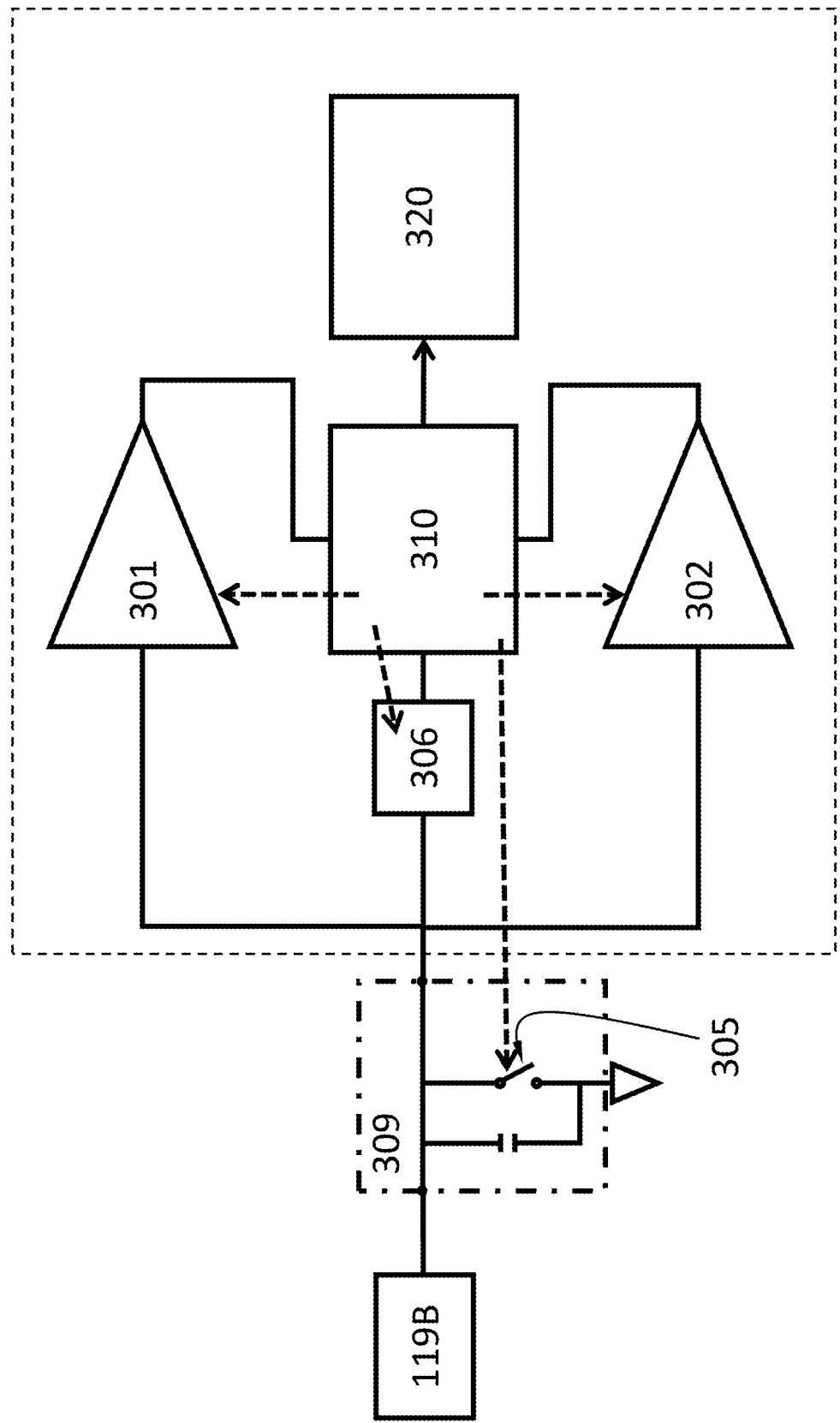

FIG. 5A and FIG. 5B each show a component diagram of the electronic system 121, according to an embodiment. The electronic system 121 may include a first voltage comparator 301, a second voltage comparator 302, a counters 320, a switch 305, an optional voltmeter 306, an integrator 309 and a controller 310.

The first voltage comparator 301 is configured to compare the voltage of at least one of the electric contacts 119B to a first threshold, according to an embodiment. The first voltage comparator 301 may be configured to monitor the voltage directly, or to calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident photon of X-ray may generate on the electric contact 119B. The maximum voltage may depend on the energy of the incident photon of X-ray, the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident photon of X-ray may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident photons of X-rays. However, having a high speed is often at the cost of power consumption.

The counter 320 is configured to register at least a number of photons of X-rays incident on the pixel 150. The counter 320 may be a software component (e.g., a number stored in a computer memory) or a hardware component (e.g., a 4017 IC and a 7490 IC). When the energy of an incident photon of X-ray is determined by the controller 310 to be in the bin the counter 320 is associated with, the number registered in the bin of counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold), according to an embodiment. The absolute value may be used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the numbers registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include the integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 6:
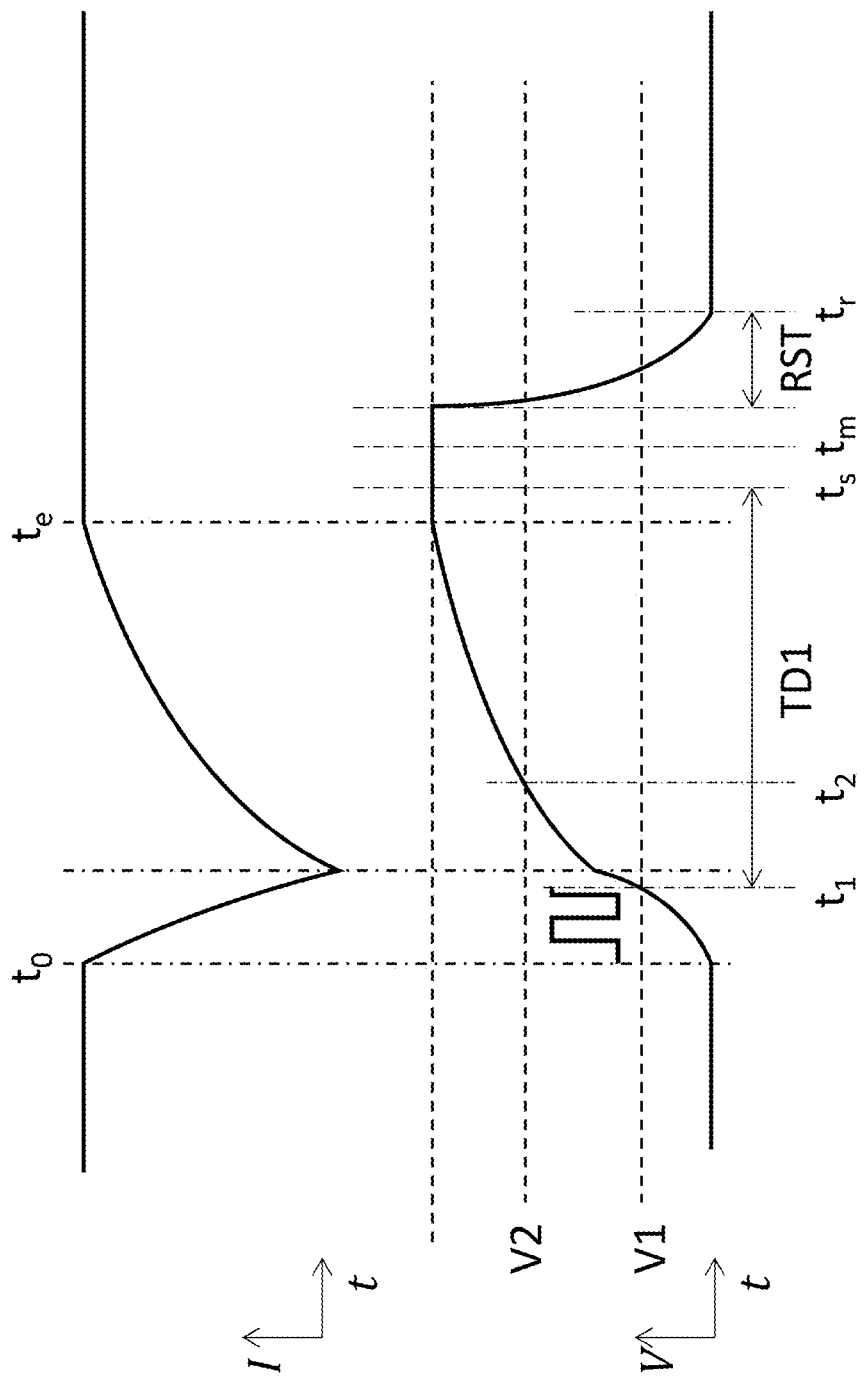
FIG. 6 schematically shows a temporal change of an electric current caused by charge carriers generated by an incident photon of X-ray, and a corresponding temporal change of a voltage, according to an embodiment.

FIG. 6 schematically shows a temporal change of the electric current flowing through the electric contact 119B

(upper curve) caused by charge carriers generated by a photon of X-ray incident on the pixel 150 encompassing the electric contact 119B, and a corresponding temporal change of the voltage of the electric contact 119B (lower curve). The voltage may be an integral of the electric current with respect to time. At time to, the photon of X-ray hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the photon of X-ray drift out of the X-ray absorption layer 110. At time $t_s$, the time delay TD1 expires. At or after time $t_e$, the controller 310 causes the voltmeter 306 to digitize the voltage and determines which bin the energy of the photon of X-ray falls in. The controller 310 then causes the number registered by the counter 320 corresponding to the bin to increase by one. In the example of FIG. 6, time $t_s$ is after time $t_e$; namely TD1 expires after all charge carriers generated by the photon of X-ray drift out of the X-ray absorption layer 110. If time $t_e$ cannot be easily measured, TD1 can be empirically chosen to allow sufficient time to collect essentially all charge carriers generated by a photon of X-ray but not too long to risk have another incident photon of X-ray. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the photon of X-ray, which relates to the energy of the photon of X-ray. The controller 310 may be configured to determine the energy of the photon of X-ray, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident photon of X-ray. If the first voltage comparator 301 has been deactivated, the controller 310 can activate it at any time before RST expires. If the controller 310 has been deactivated, it may be activated before RST expires.

Figure 7:
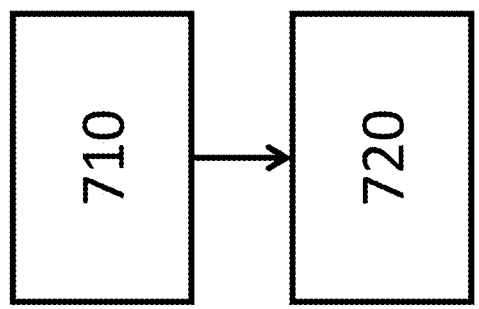
FIG. 7 shows a flowchart for a method, according to an embodiment.

FIG. 7 shows a flowchart for a method using XRF with total external reflection (TER) configuration, according to an embodiment. In procedure 710, as schematically shown in FIG. 2, the X-ray beam 102 is directed toward the surface 104 at the glancing angle 108 so that the X-ray beam 102 undergoes total external reflection by the surface 104. In procedure 720, the characteristic X-rays 109 emitted from the first element 911 is received, with the X-ray detector 100, but the X-ray detector 100 does not receive the X-ray beam 103 reflected by the surface 104, as shown in FIG. 2. If the second biological analyte 920 is present on the surface 104, the X-ray detector 100 receives a combination of the characteristic X-rays of the first element 911 and the characteristic X-rays of the second element 921.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
   an X-ray source;
   an X-ray detector;
   wherein the X-ray source is configured to direct an X-ray beam toward a surface at a glancing angle at which the X-ray beam undergoes total external reflection by the surface;
   wherein a first biological analyte is immobilized to the surface and a first element is attached to the first biological analyte;
   wherein the X-ray beam is capable of causing emission of characteristic X-rays of the first element;
   wherein the X-ray detector is configured to receive the characteristic X-rays of the first element but not the X-ray beam reflected by the surface;
   wherein the X-ray beam directed to the surface is a fan beam.

2. The apparatus of claim 1, further comprising the surface.

3. The apparatus of claim 1, wherein the surface is an external surface of a substrate.

4. The apparatus of claim 1, wherein the surface is an external surface of a film with a thickness less than 10 micrometers; wherein the film is a metal film or an epitaxial silicon film.

5. The apparatus of claim 1, wherein no X-ray beam from the X-ray source incident on the surface does not undergo total external reflection at the surface.

6. The apparatus of claim 1, further comprising a slit or a collimator in front of the X-ray source.

7. The apparatus of claim 1, wherein the X-ray detector is configured to detect the first element by determining energies of photons of the characteristic X-rays of the first element.

8. The apparatus of claim 1, wherein the surface is not at an interface with a liquid.

9. The apparatus of claim 2, further comprising the first biological analyte.

10. The apparatus of claim 1, further comprising a filter configured to prevent photons of X-ray having energies above a threshold and emitted by the X-ray source from reaching the surface.

11. The apparatus of claim 1, wherein the X-ray detector is configured not to distinguish photons of the X-ray beam and photons of the characteristic X-rays of the first element.

12. The apparatus of claim 1, wherein the X-ray beam is capable of causing emission of characteristic X-rays of a second element attached to a second biological analyte immobilized to the surface; wherein the X-ray detector is configured to receive a combination of the characteristic X-rays of the first element and the characteristic X-rays of the second element; wherein the X-ray detector is configured to detect the second element by determining energies of photons of the characteristic X-rays of the second element.

13. A method comprising:
directing an X-ray beam toward a surface at a glancing angle so that the X-ray beam undergoes total external reflection by the surface, wherein a first biological analyte is immobilized to the surface and a first element is attached to the first biological analyte and wherein the X-ray beam causes emission of characteristic X-rays of the first element;
receiving, with an X-ray detector, the characteristic X-rays of the first element but not the X-ray beam reflected by the surface;
wherein the X-ray beam is a fan beam.

14. The method of claim 13, wherein the X-ray detector is configured to detect the first element by determining energies of photons of the characteristic X-rays of the first element.

15. The method of claim 13, wherein the X-ray detector is configured not to distinguish between photons of the X-ray beam and photons of the characteristic X-rays of the first element.

16. The method of claim 13, wherein the surface is not at an interface with a liquid.

17. The method of claim 13, wherein no X-ray beam from the X-ray source incident on the surface does not undergo total external reflection at the surface.

18. The method of claim 13, wherein the surface is an external surface of a substrate.

19. The method of claim 13, wherein the surface is an external surface of a film with a thickness less than 10 micrometers; wherein the film is a metal film or an epitaxial silicon film.

20. The method of claim 13, wherein the X-ray beam causes emission of characteristic X-rays of a second element attached to a second biological analyte immobilized to the surface; wherein the X-ray detector receives a combination of the characteristic X-rays of the first element and the characteristic X-rays of the second element; wherein the X-ray detector is configured to detect the second element by determining energies of photons of the characteristic X-rays of the second element.

* * * * *